United States Patent
Akiyama et al.

(12)

(10) Patent No.: US 6,663,883 B1
(45) Date of Patent: Dec. 16, 2003

(54) MATRIX ADHERING TO NASAL MUCOSA

(75) Inventors: Yoko Akiyama, Omihachiman (JP);
Naoki Nagahara, Kawabe-gun (JP);
Hiroto Bando, Osaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 24 days.

(21) Appl. No.: 10/069,072

(22) PCT Filed: Aug. 25, 2000

(86) PCT No.: PCT/JP00/05739
§ 371 (c)(1),
(2), (4) Date: Feb. 21, 2002

(87) PCT Pub. No.: WO01/15735
PCT Pub. Date: Mar. 8, 2001

(30) Foreign Application Priority Data

Aug. 26, 1999 (JP) ............................................. 11/240162

(51) Int. Cl.⁷ ................................................. A61F 13/00
(52) U.S. Cl. ........................ 424/434; 424/421; 424/484
(58) Field of Search ................................ 424/434, 421, 424/484

(56) References Cited

U.S. PATENT DOCUMENTS

| | | | |
|---|---|---|---|
| 5,723,143 A | 3/1998 | Jacques et al. | 424/435 |
| 5,731,006 A | 3/1998 | Akiyama et al. | 424/502 |

FOREIGN PATENT DOCUMENTS

| | | |
|---|---|---|
| EP | 0 514 008 | 11/1992 |
| EP | 0 516 141 | 12/1992 |
| EP | 95/05163 | 2/1995 |
| EP | 642797 | 3/1995 |
| WO | 98/42311 | 10/1998 |
| WO | 98/42323 | 10/1998 |

*Primary Examiner*—Jyothsan Venkat
(74) *Attorney, Agent, or Firm*—Wenderoth, Lind & Ponack, L.L.P.

(57) ABSTRACT

This invention provides a matrix adhering to the nasal mucosa which allows improved transfer into the brain of a drug exerting its effect in the brain and is capable of continuously supplying the drug into the brain. This matrix contains a polyglycerol fatty acid ester, the drug exerting its effect in the brain, and a viscogenic substance.

2 Claims, No Drawings

MATRIX ADHERING TO NASAL MUCOSA

This application is a 371 of PCT/JP00/05739 filed Aug. 25, 2000.

TECHNICAL FIELD

The present invention relates to a matrix adhering to the nasal mucosa, which allows improved transfer, into the brain, of a drug exerting its effect in the brain and is capable of continuously supplying the drug into the brain.

BACKGROUND ART

As those literatures that disclose pharmaceutical compositions adsorbed into mucosae, the followings are known.
1) WO-A 98/42323 describes "A pharmaceutical composition comprising an unease inhibitor and an oil base material", and there is an example of an agent adhering to mucosae on digestive tracts.
2) JP-A 5-132416 describes "A matrix adhering to mucosae on digestive tracts and being solid at ordinary temperature, wherein a material rendered viscous with water is dispersed in the vicinity of at least surface layers of matrix particles containing a polyglycerol fatty acid ester or lipid and an active ingredient".
3) JP-A 10-324643 describes "A pharmaceutical composition adhering to mucosae on digestive tracts, which comprises a swelling agent for a material rendered viscous with water".

On the other hand, as those literatures that disclose pharmaceutical compositions adhering to the nasal mucosa, the followings are known.
4) JP-A 56-100714 describes "A preparation adhering to mucosae on the oral or nasal cavity, wherein a drug layer comprising an ointment base material containing a drug and a surfactant is unevenly distributed in a mucosa-adhesive coating layer consisting of a cellulose ether and/or an acrylate polymer or a pharmaceutically acceptable salt thereof."
5) JP-A 7-316038 describes "A pharmaceutical composition for administration into mucosae, which comprises a) an acrylic acid-alkyl (meth)acrylate copolymer or a salt thereof, b) an alkali metal salt and/or an alkaline earth metal salt, c) a drug and d) water as essential ingredients."
6) JP-A 7-215843 discloses "A sustained release pharmacological composition adhering to biological tissues, which comprises a large number of micro-units containing at least one active ingredient and a means of regulating release of said active ingredient, wherein the micro-units do substantially not show biological adhesion before coating thereof, the respective micro-units are coated with a biologically adhering polymeric coating, the coating contains one or more physically acceptable polymers, at least one of the polymers is a biologically adhering polymer, and said coating endows the micro-units with an ability to adhere to biological tissues."
7) U.S. Pat. No. 5,723,143 describes "A solid therapeutic or hygienic composition adhering to mucosae, which is used in administration into oral or nasal mucosae."
8) WO-A 95/5163 describes "An emulsion adhering to the living body, which is useful as a pharmaceutical composition with enhanced transfer of a drug into mucosae on the living body."

When a drug exerting its action on the brain is administered into the living body, transfer of the drug into the brain is significantly restricted by the blood-brain barrier. Accordingly, there is demand for a preparation capable of allowing a drug exerting its effect in the brain to exert the effect sufficiently in the brain.

DISCLOSURE OF THE INVENTION

The present inventors made extensive study for allowing a drug exerting its effect in the brain to exert the effect sufficiently in the brain, and as a result, they unexpectedly found for the first time that when a matrix comprising a polyglycerol fatty acid ester, said drug and a viscogenic substance was created, said matrix had excellent properties as a pharmaceutical preparation, for example excellent adhesion to the nasal mucosa, improved transfer of said drug into the brain, sustained supply of the drug into the brain, etc., and on the basis of this finding, this invention was completed.

That is, this invention relates to:
(1) a matrix adhering to the nasal mucosa which allows improved transfer into the brain of a drug exerting its effect in the brain, which comprises a polyglycerol fatty acid ester, the drug exerting its effect in the brain, and a viscogenic substance;
(2) the matrix according to the above-mentioned (1), wherein the polyglycerol fatty acid ester is an ester of a polyglycerol having a polymerization degree of 2 to 20 with a fatty acid having 12 to 22 carbon atoms;
(3) the matrix according to the above-mentioned (1), wherein the HLB of the polyglycerol fatty acid ester is 1 to 9;
(4) the matrix according to the above-mentioned (1), which comprises about 40 to about 95% by weight of the polyglycerol fatty acid ester;
(5) the matrix according to the above-mentioned (1), wherein the viscogenic substance is an acrylate type polymer or a salt thereof;
(6) the matrix according to the above-mentioned (5), wherein the molecular weight of the acrylate type polymer or a salt thereof is 1,000,000 to 6,000,000;
(7) the matrix according to the above-mentioned (1), which comprises about 4 to about 30% by weight of the viscogenic substance;
(8) the matrix according to the above-mentioned (1), which further comprises a swelling agent for the viscogenic substance;
(9) the matrix according to the above-mentioned (8), wherein the swelling agent for the viscogenic substance is curdlan and/or low-substituted hydroxypropylmethyl cellulose;
(10) the matrix according to the above-mentioned (1), which further comprises lipid;
(11) the matrix according to the above-mentioned (1), wherein the drug exerting its effect in the brain is a drug hardly transferring into the brain;
(12) the matrix according to the above-mentioned (1), wherein the drug exerting its effect in the brain is a sedative-hypnotic agent, an anti-anxiety agent, an antidepressant agent or an agent for treating Alzheimer's disease;
(13) the matrix according to the above-mentioned (1), wherein the drug exerting its effect in the brain is a compound having a melatonin receptor antagonist action;
(14) the matrix according to the above-mentioned (1), wherein the drug exerting its effect in the brain is a compound represented by the formula:

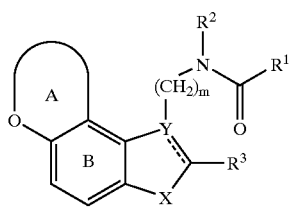

wherein R¹ is a hydrocarbon group which may have a substituent group, an amino group which may have a substituent group or a heterocyclic group which may have a substituent group, R² is a hydrogen atom or a hydrocarbon group which may have a substituent group, R³ is a hydrogen atom or a hydrocarbon group which may have a substituent group or a heterocyclic group which may have a substituent group, X is $CHR^4$, $NR^4$, O or S whereupon $R^4$ represents a hydrogen atom or a hydrocarbon group which may have a substituent group, Y is C, CH or N provided that when X represents $CH_2$, Y is C or CH, ═══ is a single or double bond, ring A is a 5- to 7-memberred, oxygen atom-containing heterocyclic ring which may have a substituent group, ring B is a benzene ring which may have a substituent group, and m is an integer of 1 to 4; or a salt thereof;

(15) the matrix according to the above-mentioned (1), wherein the drug exerting its effect in the brain is (S)-N-[2-(1,6,7,8-tetrahydro-2H-indeno[5,4-b]furan-8-yl)ethyl] propionamide;

(16) the matrix according to the above-mentioned (1), wherein the drug exerting its effect in the brain is (S)-N-[2-(1,6,7,8-tetrahydro-2H-indeno[5,4-b]furan-8-yl)ethyl] acetamide;

(17) the matrix according to the above-mentioned (1), which comprises about 0.1 to about 50% by weight of the drug exerting its effect in the brain;

(18) a solid preparation comprising the matrix described in the above-mentioned (1);

(19) the solid preparation according to the above-mentioned (18), which is finely divided particles or powder;

(20) the solid preparation according to the above-mentioned (19), which is spherical;

(21) the solid preparation according to the above-mentioned (19), which has a particle diameter of about 0.1 to about 100 μm;

(22) a method of improving transfer, into the brain, of a drug exerting its effect in the brain, which comprises using a matrix comprising a polyglycerol fatty acid ester, said drug and a viscogenic substance; and

(23) use of a polyglycerol fatty acid ester, a drug exerting its effect in the brain, and a viscogenic substance in producing a matrix adhering to the nasal mucosa which allows improved transfer of said drug into the brain.

In this invention, the polyglycerol fatty acid ester may be any one of monoesters, diesters and polyesters insofar as they are esters of polyglycerols with fatty acids. The polyglycerol fatty acid ester is characterized in that it does not show crystalline polymorphism and hardly interacts with a drug so that even if the drug is coexistent therewith, the drug is hardly inactivated and is thus stable for a prolonged period of time.

The polyglycerol is "a polyvalent alcohol having "n" (cyclic) to "n+2" (linear or branched) hydroxyl groups and "n−1" (linear or branched) to "n" (cyclic) ether linkages in one molecule" ("Polyglycerol Ester" edited by Sakamoto Yakuhin Kogyo Co., Ltd. and published on Oct. 4, 1994), and may be linear or branched. As the polyglycerol, use can be made of e.g. those compounds represented by:

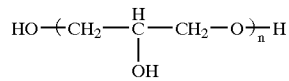

wherein n, degree of polymerization, is an integer of 2 or more. n is usually 2 to 50, preferably 2 to 20 and more preferably 2 to 10. Examples of such polyglycerols include diglycerol, triglycerol, tetraglycerol, pentaglycerol, hexaglycerol, heptaglycerol, octaglycerol, nonaglycerol, decaglycerol, pentadecaglycerol, eicosaglycerol, triacontaglycerol etc. Among these polyglycerols, for example tetraglycerol, hexaglycerol, decaglycerol etc. are preferable.

As the fatty acid, for example fatty acids each containing 8 to 40 carbon atoms, preferably 12 to 22 carbon atoms, are exemplified. The fatty acid may be saturated or unsaturated, and includes e.g. palmitic acid, stearic acid, oleic acid, linolic acid, linolenic acid, myristic acid, lauric acid, ricinoleic acid, caprylic acid, capric acid, behenic acid etc. Among these, e.g. stearic acid, oleic acid, lauric acid, linolic acid, behenic acid etc. are preferable.

Examples of the polyglycerol fatty acid ester include e.g. behenic acid hexa(tetra)glyceride, behenic acid dodeca(deca)glyceride, behenic acid octa(hexa)glyceride, caprylic acid mono(deca)glyceride, caprylic acid di(tri)glyceride, capric acid di(tri)glyceride, lauric acid mono(tetra)glyceride, lauric acid mono(hexa)glyceride, lauric acid mono(deca)glyceride, oleic acid mono(tetra)glyceride, oleic acid mono(hexa)glyceride, oleic acid mono(deca)glyceride, oleic acid di(tri)glyceride, oleic acid di(tetra)glyceride, oleic acid sesqui(deca)glyceride, oleic acid penta(tetra)glyceride, oleic acid penta(hexa)glyceride, oleic acid deca(deca)glyceride, linolic acid mono(hepta)glyceride, linolic acid di(tri)glyceride, linolic acid di(tetra)glyceride, linolic acid di(hexa)glyceride, stearic acid mono(di)glyceride, stearic acid mono(tetra)glyceride, stearic acid mono(hexa)glyceride, stearic acid mono(deca)glyceride, stearic acid tri(tetra)glyceride, stearic acid tri(hexa)glyceride, stearic acid sesqui(hexa)glyceride, stearic acid penta(tetra)glyceride, stearic acid penta(hexa)glyceride, stearic acid deca(deca)glyceride, palmitic acid mono(tetra)glyceride, palmitic acid mono(hexa)glyceride, palmitic acid mono(deca)glyceride, palmitic acid tri(tetra)glyceride, palmitic acid tri(hexa)glyceride, palmitic acid sesqui(hexa)glyceride, palmitic acid penta(tetra)glyceride, palmitic acid penta(hexa)glyceride, palmitic acid deca(deca)glyceride etc. One or more, preferably two or three of the above polyglycerol fatty acid esters may be mixed and used in an arbitrary ratio.

The molecular weight of the polyglycerol fatty acid ester is usually about 200 to about 7000, preferably about 300 to about 3000 and more preferably about 500 to about 3000.

The HLB (hydrophile-lipophile balance) of the polyglycerol fatty acid ester is usually 1 to 22, preferably 1 to 15 and more preferably 1 to 9. The HLB may be adjusted as desired by suitably mixing two or more polyglycerol fatty acid esters which are different in HLB. By adjusting the HLB of the polyglycerol fatty acid ester, the releasability and dissolution of the drug can be controlled.

Although the melting point of the polyglycerol fatty acid ester is also varied depending on the type of the drug and the viscogenic substance, the melting point is e.g. about 15 to about 80° C., preferably about 30 to about 75° C. and more preferably about 45 to about 75° C.

The polyglycerol fatty acid ester usually used in this invention is solid at ordinary temperature (15° C.), but insofar as the matrix adhering to the nasal mucosa is solid at ordinary temperature, a polyglycerol fatty acid ester which is liquid at ordinary temperature may also be used.

The polyglycerol fatty acid ester is preferably an ester of a polyglycerol having a polymerization degree of 2 to 20 with a fatty acid having 12 to 22 carbon atoms.

Preferable examples of the polyglycerol fatty acid ester include e.g. behenic acid hexa(tetra)glyceride (for example, trade name: Poem J-46B produced by Riken Vitamin Co., Ltd.; trade name: HB-310 produced by Sakamoto Yakuhin Kogyo, etc.), behenic acid dodeca(deca)glyceride (for example, trade name: OB-500 produced by Sakamoto Yakuhin Kogyo Co., Ltd., etc.), behenic acid octa(hexa)glyceride (for example, trade name: DB-750 produced by Sakamoto Yakuhin Kogyo Co., Ltd., etc.), stearic acid penta(tetra) glyceride (for example, trade name: PS-310 produced by Sakamoto Yakuhin Kogyo Co., Ltd., etc.), stearic acid mono(tetra)glyceride (for example, trade name: MS-310 produced by Sakamoto Yakuhin Kogyo Co., Ltd., etc.), stearic acid penta(hexa)glyceride (for example, trade name: PS-500 produced by Sakamoto Yakuhin Kogyo Co., Ltd., etc.), stearic acid sesqui(hexa)glyceride (for example, trade name: SS-500 produced by Sakamoto Yakuhin Kogyo Co., Ltd., etc.), stearic acid deca(deca)glyceride (for example, trade name: DAS-750 produced by Sakamoto Yakuhin Kogyo Co., Ltd., etc.), stearic acid mono(hexa)glyceride (for example, trade name: PO-500 produced by Sakamoto Yakuhin Kogyo Co., Ltd., etc.), oleic acid penta(tetra)glyceride (for example, trade name: PO-310 produced by Sakamoto Yakuhin Kogyo Co., Ltd., etc.), oleic acid deca(deca)glyceride (for example, trade name: DAO-750 produced by Sakamoto Yakuhin Kogyo Co., Ltd., etc.), stearic acid mono(deca)glyceride, polyglycerol-condensed ricinoleic acid ester [polyglycerol polyricinolate, for example, tetraglycerol polyricinolate (for example, trade name: CRS-75 produced by Sakamoto Yakuhin Kogyo Co., Ltd., etc.)] or the like. Two or more, preferably two or three of the above polyglycerol fatty acid esters may be mixed and used in an arbitrary ratio.

The content of the polyglycerol fatty acid ester in the matrix adhering to the nasal mucosa is for example about 5 to about 98% by weight, preferably about 20 to about 95% by weight and more preferably about 40 to about 95% by weight.

The polyglycerol fatty acid ester is used in an amount of about 0.01 to about 10000 parts by weight, preferably about 0.1 to about 1000 parts by weight, relative to 1 part by weight of the drug exerting its effect in the brain.

The matrix adhering to the nasal mucosa according to this invention may further contain lipid. Use is made of lipid having a melting point of about 40 to about 120° C., preferably about 40 to about 90° C. The lipid include e.g. $C_{14-22}$ saturated fatty acids (for example, myristic acid, palmitic acid, stearic acid, behenic acid etc.) or salts thereof (for example, sodium salts, potassium salts); $C_{16-22}$ higher alcohols (for example, cetyl alcohol, stearyl alcohol etc.); fatty acid glycerol esters, that is, monoglycerides, diglycerides and triglycerides with the above fatty acids (for example, 1-monostearin, 1-monopalmitin etc.); fats and oils (for example, soybean oil, olive oil, rapeseed oil, peppermint oil, sesame oil, castor oil, camellia oil, wheat malt oil, fennel oil, corn oil, sunflower oil, cottonseed oil, coconut oil, peanut oil and hardened oils thereof, tallow, lard etc.); wax (for example, beeswax, carnauba wax, spermaceti, white wax etc.); hydrocarbons (for example, paraffin, microcrystalline wax etc.); phospholipid (for example, hydrogenated lecithin etc.), etc. Among these lipids, for example fats and oils, wax, $C_{14-22}$ saturated fatty acids, $C_{16-22}$ higher alcohols, hydrocarbons etc. are preferable, and hardened cottonseed oil, hardened castor oil, hardened soybean oil, carnauba wax, stearic acid, stearyl alcohol, microcrystalline wax etc. are more preferable. In particular, hardened castor oil, carnauba wax etc. are preferable.

When the polyglycerol fatty acid ester is used in combination with lipid, the lipid is preferably fats and oils (preferably hardened oils) and wax.

Specific combination of the polyglycerol fatty acid ester and the lipid includes e.g. combinations of at least one member selected from behenic acid hexa(tetra)glyceride, behenic acid dodeca(deca)glyceride, behenic acid octa(hexa)glyceride, stearic acid penta(tetra)glyceride and stearic acid penta(hexa)glyceride and at least one member selected from hardened castor oil, carnauba wax and microcrystalline wax.

When the polyglycerol fatty acid ester is used in combination with the lipid, the content of the two components in the matrix adhering to the nasal mucosa, or the ratio thereof to the drug exerting its effect in the brain, shall be identical with the content or the ratio of the polyglycerol fatty acid ester when used singly.

In this invention, the viscogenic substance means a pharmaceutically acceptable substance which is rendered viscous with water to show adhesion to the nasal mucosa. In particular, a substance swelling with water and imparted with significantly increased viscosity with water is preferable. The viscogenic substance includes e.g. a polymer, a naturally occurring viscogenic substance, etc.

2% aqueous solution of said polymer at 20° C. has a viscosity of about 3 to about 50000 cps, preferably about 10 to about 30000 cps and more preferably about 15 to about 30000 cps. In the case of a polymer thickening upon neutralization, 0.2% neutralized solution thereof at 20° C. has a viscosity of about 100 to about 500000 cps, preferably about 100 to about 200000 cps and more preferably about 1500 to about 100000 cps.

The viscosity of the viscogenic substance shall be determined at 20° C. with a Brookfield viscometer.

The polymer is preferably an acidic polymer, and the acidic polymer includes polymers having carboxyl groups, sulfo groups or salts thereof. In particular, the polymer having carboxyl groups or salts thereof is preferable.

The polymer having carboxyl groups or salts thereof includes e.g. acrylate type polymers (including copolymers)

comprising acrylic acid as a constituent monomer, or salts thereof. The salts include monovalent metal salts such as sodium and potassium salts; and divalent metal salts such as magnesium and calcium salts. The acrylate type polymer or salts thereof include polymers containing about 58 to about 63% by weight of carboxyl groups and having molecular weights of about 200,000 to 6,000,000, preferably 1,000,000 to 6,000,000, more preferably 1,000,000 to 5,000,000. Preferable acrylate type polymers and salts thereof include acrylate homopolymers and salts thereof. The acrylate polymer containing about 58 to about 63% by weight of carboxyl groups is described as carboxy vinyl polymer in Non-Pharmaceutical Ingredient Standards in Japanese Pharmacopoeia (October, 1986). Examples of said polymer include e.g. Carbomer (trade name: Carbopol produced by The B. F. Goodrich Company) 940, 934, 934P, 941, 1342, 974P (NF XVIII) etc.; HIVISWAKO 103, 104, 105 (trade name, produced by Wako Pure Chemical Industries, Ltd.), NOVEON AA1 (trade name, produced by The B.F. Goodrich Company), calcium polycarbofil (USP XXIII) etc.

The naturally occurring viscogenic substance includes e.g. mucin, agar, gelatin, pectin, carrageenan, sodium alginate, locust bean gum, xanthane gum, tragacanth gum, gum arabic, chitosan, pullulan, waxy starch, sucralfate, cellulose and derivatives thereof (for example, hydroxypropyl cellulose, hydroxypropylmethyl cellulose, cellulose sulfate etc.). In particular, hydroxypropyl cellulose, hydroxypropylmethyl cellulose etc. are preferable.

Two or more naturally occurring viscogenic substances described above may be mixed and used in an arbitrary ratio.

The viscogenic substance is preferably an acrylate type polymer or a salt thereof.

The content of the viscogenic substance in the matrix adhering to the nasal mucosa is for example about 0.005 to about 99% by weight, preferably about 0.5 to about 45% by weight and more preferably about 4 to about 30% by weight.

The matrix adhering to the nasal mucosa according to this invention may further contain a swelling agent for the viscogenic substance. The swelling agent for the viscogenic substance refers to a pharmaceutically acceptable substance swelling the viscogenic substance or promoting swelling of the viscogenic substance with water. The swelling agent can be used to provide the matrix adhering to the nasal mucosa which is excellent in adhesion to the nasal mucosa and can be retained in the nasal mucosa for a prolonged period of time.

The swelling agent for the viscogenic substance includes e.g. curdlan and low-substituted hydroxypropylmethyl cellulose.

Curdlan is a linear water-insoluble polysaccharide ($\beta$-1, 3-glucan) produced by a microorganism (Alcaligenes faecalis var. myxogenes), and particularly curdlan N (food additive) can be used preferably.

The low-substituted hydroxypropyl cellulose (Japanese Pharmacopoeia, 12th revised edition) is prescribed as follows: alcohol groups on the cellulose have been replaced by hydroxypropoxy groups, and the content of the hydroxypropyl groups (% by weight) is 5.0 to 16.0%. It is possible to use a wide variety of such cellulose having a content of substituent groups in this range and a varying particle size, for example, LH-11 (hydroxypropoxyl group content: 10.0 to 13.0% by weight; particle size: 98% by weight or more particles pass through a screen of 150 $\mu$m in mesh size, and 0.5% by weight or less particles are on a screen of 180 $\mu$m in mesh size), LH-20 (hydroxypropoxyl group content: 13.0 to 16.0% by weight; particle size: 90% by weight or more pass through a screen of 75 $\mu$m, and 1.0% by weight or less are on a screen of 106 $\mu$m), LH-21 (hydroxypropoxyl group content: 10.0 to 13.0% by weight; particle size: 90% by weight or more pass through a screen of 75 $\mu$m, and 1.0% by weight or less are on a screen of 106 $\mu$m), LH-22 (hydroxypropoxyl group content: 7.0 to 10.0% by weight; particle size: 90% by weight or more pass through a screen of 75 $\mu$m, and 1.0% by weight or less are on a screen of 106 $\mu$m) and LH-31 (hydroxypropoxyl group content: 10.0 to 13.0% by weight; average particle diameter 30 $\mu$m or less; particle size: 50% by weight or more pass through a screen of 45 $\mu$m, and 5.0% by weight or less are on a screen of 75 $\mu$m). In particular, LH-22 and LH-31 are preferable.

The content of the swelling agent for the viscogenic substance in the matrix adhering to the nasal mucosa is for example about 0.5 to about 50% by weight, preferably about 1 to about 50% by weight and more preferably about 1 to about 30% by weight.

In this invention, the drug exerting its effect in the brain (also referred simply to hereinafter as the drug) includes e.g. the following compounds, hormones, peptides, proteins etc. acting via the nerve center: antiinflammatory agents such as naproxen sodium, isopropyl antipyrine, ibuprofen, ketoprofen and diclofenac; sympathetic nervous agonists such as ephedrine hydrochloride, salbutamol sulfate, and phenylpropanolamine hydrochloride; antihistamines such as chlorpheniramine maleate, diphenhydramine hydrochloride, and clemastine fumarate; antibiotics such as amoxicillin, cephalexin, clarisromycin and chloxasilin sodium antitumor agents such as fluorouracil, cisplatin and methotrexate; anti-epileptic agents such as phenytoin sodium, ethosuximide, and sodium valproate; choline agonists such as bethanechol hydrochloride, neostigmine bromide, and carbachol; opioid compounds such as morphine hydrochloride, morphine sulfate, oxycodone, codeine, buprenorphine, and fentanyl; sedative-hypnotic agents or antianxiety agents such as melatonin, diazepam, and chlordiazepoxide; antidepressant agents such as fluoxetin, sertraline, paroxetine, Venlafaxine, nefazodone, reboxetine, imipramine hydrochloride and duloxetine; anesthetics such as droperidol and halothane; anti-Parkinson drugs such as dopamine, L-dopa, and apomorphine; drugs for mind and nerves, such as haloperidol, prochlorperazin; cerebral circulation-ameliorating drugs such as vinpocetine; drugs for treating schizophrenia, such as olanzapine, risperidone, quetiapine and iloperidone; intelligence improvers; drugs for treating migraines, such as dihydroergotamine, sumatriptan, butrophanol, and capsaicin; skeletal muscle-relaxing drugs; agents for treating Alzheimer's disease, such as tacrine and donepezil; agents for treating alcoholism; auxiliary agents for quitting smoking; agents for treating drug abuse; vomiting-controlling drugs; drugs for the central nervous system, such as idebenone, indeloxazine hydrochloride, bifemelane hydrochloride, protirelin tartrate, and baclofen; neurotransmitters and related substances, such as acetyl choline, $\gamma$-aminobutyric acid, serotonin, β-endorphin, methionine-enkephalin, Substance P, glycine, glutamic acid, aspartic acid, vasoactive intestinal polypeptide (VIP), epinephrine, norepinephrine and neurotensin; peptides released from the hypothalamus and involved in hormone synthesis and secretion, such as thyrotropin-releasing hormone (TRH), corticotropin-releasing hormone (CRH), luteinizing hormone-releasing hormone (LHRH), follicle-stimulating hormone-releasing hormone (FSHRH), prolactin-releasing hormone (PrRH), growth hormone-releasing hormone (GRH), somatostatin, galanin, galanin-like peptide (GALP), neuromedin U, ghrelin, apelin, urotensin II, orexin, and their related compounds such as agonists and antagonists, for example leuprorelin; pituitary hormones such as thyroid-stimulating hormone (TSH), adrenocorticotropic hormone (ACTH), luteinizing hormone (LH), follicle-stimulating hormone (FSH), prolactin (PRL), growth hormone (GH), vasopressin, oxytocin and neuropeptide Y; thyroid hormone; parathyroid hormone (PTH); saccharide metabolism-related hormones such as insulin and glucagon; adrenocorticotropic medulla-related peptides such as angiotensin, dehydroepiandrosterone; alimentary canal hormones such as gastrin, secretin, cholecystokinin and motilin; neuropeptides involved in appetite regulation, such as leptin, melanin concentrating hormone (MCH), opioid, cholecystokinin, bombesin, and their related compounds such as agonists and antagonists; and compounds related to instinctive behaviors and body temperature.

Out of these drugs, those drugs which upon administration into blood vessels, digestive tracts, lungs, skin etc., undergo significant restriction of transfer thereof to the brain because of their degradation with gastric acid or enzyme, metabolism by the initial passage effect, or the blood-brain barrier (that is, drugs hardly transferring into the brain), or exhibit side-effects because of an increase in their blood levels can be effectively used in the matrix adhering to the nasal mucosa according to this invention.

In the matrix adhering to the nasal mucosa, the content of the drug exerting its effect in the brain is for example about 0.005 to about 95% by weight, preferably about 0.1 to about 90% by weight, more preferably about 0.1 to about 50% by weight.

The drug exerting its effect in the brain is preferably is a sedative-hypnotic agent, an anti-anxiety agent, an antidepressant agent or an agent for treating Alzheimer's disease.

For example, such drugs are preferably compounds having a melatonin receptor agonist action. The compounds having a melatonin receptor agonist action are not particularly limited insofar as they have such action, and for example, such melatonin agonists or antagonists thereof include:

(1) compounds described in EP-A-578620, represented by the formula:

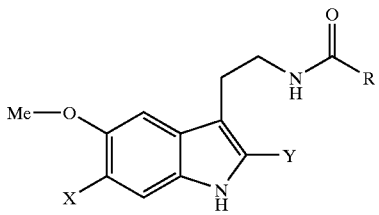

X = H, Y = Br, R = Me
X = H, Y = I, R = Me
X = Cl, Y = H, R = Me
X = H, Y = CH$_3$, R = cyclopropyl (2) a compound described in U.S. Pat. No. 411,675, represented by the formula:

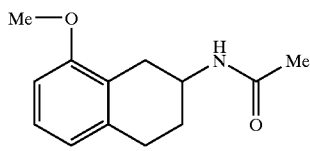

(3) a compound described in JP-A 7-048331 (EP-A-447285), represented by the formula:

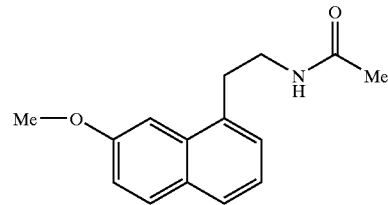

(4) a compound described in FR-014630, represented by the formula:

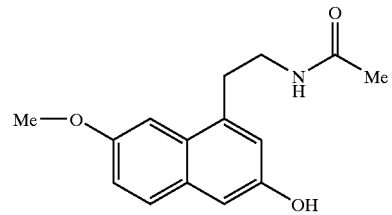

(5) a compound described in EP-A-591057, represented by the formula:

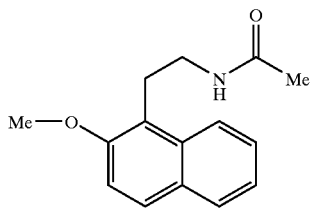

(6) compounds described in EP-A-527687, represented by the formulae:

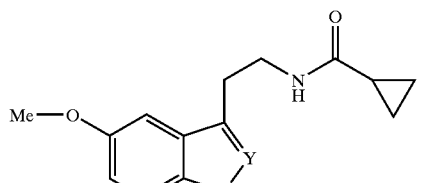

X = S, O,   Y = CH
X = O, NH,  Y = N

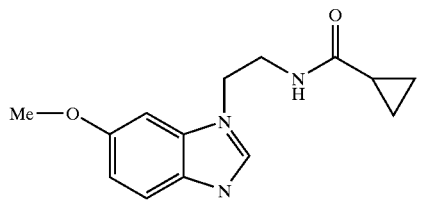

(7) compounds described in EP-A-506539, represented by the formulae:

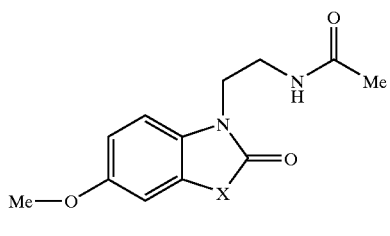

X = O, S

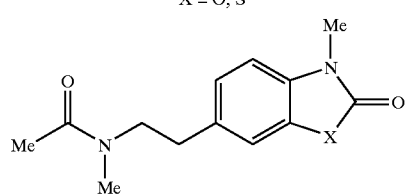

X = O, S

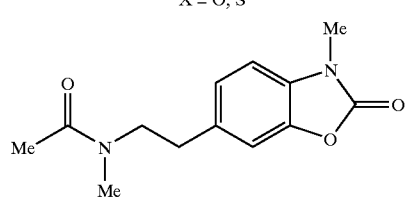

(8) compounds described in JP-A 7-196493 or JP-A 63-196563, represented by the formula:

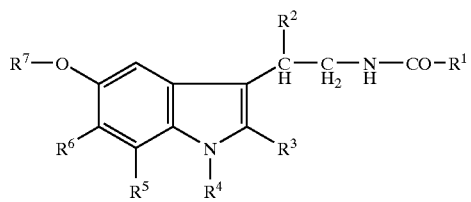

wherein $R^1$ is hydrogen, $C_{1-4}$ alkyl or $C_{1-4}$ alkoxy; $R^2$ is hydrogen or $C_{1-4}$ alkyl; $R^3$ is hydrogen, $C_{1-4}$ alkyl, phenyl or substituted phenyl; $R^4$ is hydrogen, haloacetyl, $C_{1-5}$ alkanoyl, benzoyl, or halo- or methyl-substituted benzoyl; each of $R^5$ and $R^6$ is hydrogen or halo; and $R^7$ is hydrogen or $C_{1-4}$ alkyl, provided that when $R^3$, $R^4$ and $R^5$ each are hydrogen, $R^2$ is $C_{1-4}$ alkyl;

or salts thereof, and particularly a compound (LY156735) represented by the formula:

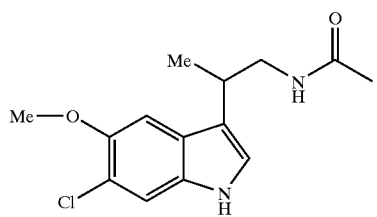

(9) compounds described in WO 97/43272, represented by the formula:

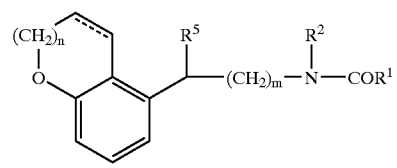

wherein $R^1$ and $R^2$ are the same or different and represent hydrogen, $C_{1-6}$ alkyl, $C_{3-7}$ cycloalkyl or aryl; $R^3$ and $R^4$ are the same or different and represent hydrogen, halogen, $C_{1-6}$ alkyl or substituted aryl; $R^5$ is hydrogen or $C_{1-6}$ alkyl; n is 0, 1 or 2; and m is 1, 2, 3 or 4;

═══ is a single or double bond, or salts thereof, and particularly a compound represented by the formula:

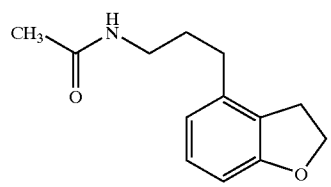

(10) compounds described in WO 98/25606, represented by the formula:

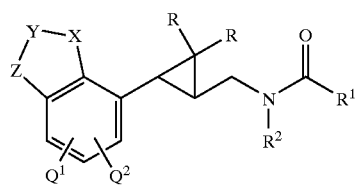

wherein each of $Q^1$ and $Q^2$ is hydrogen or halogen; X is $CH_2$, CH or oxygen; Y is $CR^3$, $CR^3R^4$ or $(CH_2)$ n (n=1-4); Z is $CH_2$, CH or oxygen; R is hydrogen, halogen or $C_{1-4}$ alkyl; m is 1 or 2; $R^1$ is $C_{1-6}$ alkyl, $C_{3-6}$ cycloalkyl, $C_{1-3}$ haloalkyl, $C_{1-6}$ alkylamino, $C_{2-6}$ alkenyl, $C_{1-4}$ alkoxy ($C_{1-4}$) alkyl, $C_{1-4}$ alkylthio ($C_{1-4}$) alkyl or trifluoromethyl alkyl; $R^2$ is hydrogen or $C_{1-4}$ alkyl; and each of $R^3$ and $R^4$ is hydrogen or $C_{1-4}$ alkyl, or salts thereof, and particularly a compound represented by the formula:

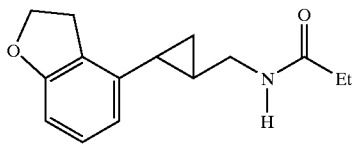

(11) compounds described in JP-A 9-507057, represented by the formula:

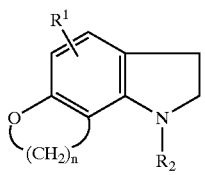

wherein $R^1$ is hydrogen, halogen or $C_{1-6}$ alkyl; $R^2$ is a group of the formula —$CR^3R^4(CH_2)_pNR^5COR^6$; $R^3$, $R^4$ and $R^5$ may be the same or different and represent hydrogen or $C_{1-6}$ alkyl; $R^6$ is $C_{1-6}$ alkyl or $C_{3-7}$ cycloalkyl; n is an integer of 2, 3 or 4; and p is an integer of 1, 2, 3 or 4;

or salts thereof, and particularly a compound represented by the formula:

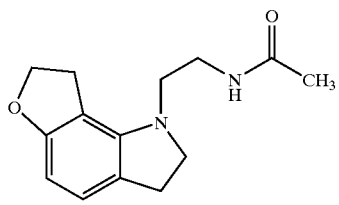

(12) compounds described in WO 97/32871, represented by the formula:

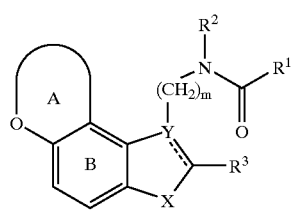

wherein $R^1$ is a hydrocarbon group which may have a substituent group, an amino group which may have a substituent group or a heterocyclic group which may have a substituent group, $R^2$ is a hydrogen atom or a hydrocarbon group which may have a substituent group, $R^3$ is a hydrogen atom, a hydrocarbon group which may have a substituent group or a heterocyclic group which may have a substituent group, X is $CHR^4$, $NR^4$, O or S whereupon $R^4$ represents a hydrogen atom or a hydrocarbon group which may have a substituent group, Y is C, CH or N provided that when X represents $CH_2$, Y is C or CH, === is a single or double bond, ring A is a 5- to 7-memberred, oxygen atom-containing heterocyclic ring which may have a substituent group, ring B is a benzene ring which may have a substituent group, and m is an integer of 1 to 4;

or salts thereof.

In particular, Compound (I) having high affinity for melatonin receptors and high selectivity particularly for $ML_1$ receptor is preferable.

Compound (I) is preferably a compound represented by the formula:

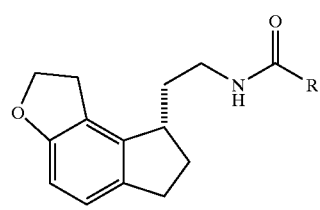

wherein R represents a $C_{1-6}$ alkyl group (methyl, ethyl, propyl, isopropyl, butyl, isobutyl, sec-butyl, tert-butyl, pentyl, hexyl etc.), and specifically Compound (I) is preferably (S)-N-[2-(1,6,7,8-tetrahydro-2H-indeno[5,4-b]furan-8-yl)ethyl] propionamide or (S)-N-[2-(1,6,7,8-tetrahydro-2H-indeno[5,4-b]furan-8-yl)ethyl] acetamide.

In this specification, the matrix means a system where the ingredients constituting the matrix have been uniformly dispersed, and is clearly distinguished from a system where the ingredients have been topically or unevenly distributed or have formed a layer, or from an emulsion or a simple mixture of the ingredients.

That is, in the matrix adhering to the nasal mucosa according to this invention, the ingredients, that is, "the polyglycerol fatty acid ester", "the drug exerting its effect in the brain" and "the viscogenic substance" have been uniformly dispersed. Further, when the matrix further contains "the lipid" and "the swelling agent for the viscogenic substance", the lipid and the swelling agent have also been uniformly dispersed.

The matrix adhering to the nasal mucosa according to this invention is excellent in adhesion to the nasal mucosa and capable of releasing "the drug exerting its effect in the brain" continuously at a predetermined rate.

The particle diameter of the matrix is preferably about 0.1 to about 1500 μm, more preferably about 0.1 to about 100 μm and most preferably about 5 to about 50 μm.

The matrix adhering to the nasal mucosa according to this invention is produced by uniformly dispersing e.g. the constituent ingredients, that is, "the polyglycerol fatty acid ester", "the drug exerting its effect in the brain" and "the viscogenic substance". When the matrix further contains "the lipid" and "the swelling agent for the viscogenic substance", the lipid and the swelling agent are also dispersed uniformly.

For example, said matrix is produced by melting the polyglycerol fatty acid ester by heating it at the melting point or more, then adding the drug or the viscogenic substance thereto simultaneously or separately and cooling the resulting mixture. When the lipid is used, the lipid is used in the same manner as for the polyglycerol fatty acid ester, and when the swelling agent for the viscogenic substance is used, the swelling agent is used in the same manner as for the viscogenic substance.

In this case, heating temperature is for example about 40 to about 150° C., preferably about 50 to about 110° C., and more preferably about 50 to about 90° C.

The heating and dispersion step described above is conducted using e.g. a conventional granulator, and the cooling step is conducted by e.g. spray cooling. This spray cooling is conducted for example by spray chilling, and in this case, a solid preparation (for example, finely divided particles) is obtained.

Spray chilling is conducted by dropping a mixture consisting of the polyglycerol fatty acid ester, the drug and the viscogenic substance at a predetermined flow rate onto a high-speed rotating disk. The rotating disk used may be a smooth disk (e.g. an aluminum disk) having a diameter of 5 to 100 cm, preferably 10 to 20 cm. The rotational speed of the rotating disk is for example 10 to 25000 rpm, preferably 3000 to 20000 rpm, more preferably 6000 to 15000 rpm. The rate of dropping the mixture is selected depending on the desired particle diameter, but is usually about 2 to 200 g/min., preferably about 5 to about 100 g/min.

The matrix of this invention obtained by this spray chilling method is approximately spherical. Therefore, a stable rate of releasing the drug can be achieved, and thus spray chilling is preferable as a method of producing the matrix of this invention.

Alternatively, the matrix adhering to the nasal mucosa according to this invention can also be produced by dispersing the constituent ingredients by kneading them in a conventional solvent (for example, methanol, acetonitrile, chloroform etc.), followed by granulation thereof.

The matrix adhering to the nasal mucosa according to this invention may be formed into a solid preparation by coating it with a coating agent containing the above viscogenic substance or pharmaceutical additives. The coating agent may further contain at least one additive selected from the swelling agent for the viscogenic substance, the polyglycerol fatty acid ester and a water-insoluble polymer.

The pharmaceutical additives may be those ordinarily used in the field of pharmaceutical manufacturing, and include e.g. excipients such as lactose, corn starch, talc, crystalline cellulose, powdery sugar, magnesium stearate, mannitol, xylitol, sorbitol, erythritol, light silicic anhydride, magnesium carbonate, calcium carbonate and L-cysteine; binders such as starch, sucrose, gelatin, powder of gum arabic, methyl cellulose, carboxymethyl cellulose, sodium carboxymethyl cellulose, hydroxypropyl cellulose, hydroxypropylmethyl cellulose, polyvinyl pyrrolidone, pullulan and dextrin; disintegrating agents such as calcium carboxymethyl cellulose, low-substituted hydroxypropyl cellulose, sodium croscarmellose, sodium carboxymethyl starch, hydroxypropyl starch and partially pregelatinized starch; surfactants such as anionic surfactants such as sodium alkyl sulfate, and nonionic surfactants such as polyoxyethylene sorbitan fatty acid esters, polyoxyethylene fatty acid esters and polyoxyethylene castor oil derivatives; acid regulators and mucosa-protecting agents such as magnesium hydroxide, magnesium oxide, aluminum hydroxide, aluminum sulfate, magnesium metasilicate aluminate, magnesium silicate aluminate and sucralfate; coloring agents; taste correctives; adsorbents; preservatives; swelling agents; and antistatic additives. The amount of these pharmaceutical additives is suitably selected in the range where the adhesion of the solid preparation to the nasal mucosa is not deteriorated.

The "water-insoluble polymer" which may be added to the coating agent includes e.g. hydroxypropylmethyl cellulose phthalate, hydroxypropylmethyl cellulose acetate succinate, carboxymethylethyl cellulose, cellulose acetate trimellitate, cellulose acetate phthalate, ethyl cellulose, aminoalkyl methacrylate copolymers [trade name: Eudragit RS-100, RL-100, RL-PO, RS-PO, RS-30D, RL-30D produced by Röhm Pharma Ltd.], methacrylic acid-ethyl acrylate copolymers [trade name: Eudragit L100-55 produced by Röhm Pharma Ltd.], methacrylic acid-methyl methacrylate copolymers [trade name: Eudragit L100, S100, L30D-55, NE-30D, produced by Röhm Pharma Ltd.] and polyvinyl acetate. Two or more of these polymers can be mixed and used in an arbitrary ratio.

The content of the viscogenic substance in the coating agent is for example about 0.005 to about 100% by weight, preferably about 0.05 to about 95% by weight and more preferably about 1 to about 10% by weight of the total solid content in the coating agent.

When the coating agent contains pharmaceutical additives, the content of the pharmaceutical additives is for example about 0.1 to about 70% by weight, preferably about 1 to about 50% by weight and more preferably about 20 to about 50% by weight of the total solid content in the coating agent.

The amount of the coating agent applied is suitably selected depending on the shape of the solid preparation, the desired adhesion to mucosae, etc. For example, when the solid preparation is in the form of granules, the amount of the coating agent applied thereon is about 0.1 to about 50% by weight, preferably about 1 to about 20% by weight, relative to the whole of the solid preparation. Further, when the solid preparation is in the form of finely divided particles, the amount of the coating agent applied thereon is about 0.1 to about 100% by weight, preferably about 1 to about 50% by weight, relative to the whole of the solid preparation.

As the coating method, it is possible to use any methods known in the art, for example pan coating, fluid coating, rolling coating etc. When the coating agent is a solution or dispersion containing water or an organic solvent, spray coating can also be used. The type of the organic solvent is not particularly limited, and use can be made e.g. alcohols such as methanol, ethanol and isopropyl alcohol; ketones such as acetone; halogenated hydrocarbons such as chloroform, dichloromethane and trichloroethane.

When the coating agent contains the polyglycerol fatty acid ester, the polyglycerol fatty acid ester and if necessary other additives may be coated by heating and melting them, then kneading and emulsifying the resultant mixture in water, spraying the resultant emulsion onto the matrix and drying it.

Further, when the coating agent contains the polyglycerol fatty acid ester, the matrix preheated with hot air in a device such as a coating pan may be coated therewith by introducing the coating agent into the device and then melting and extending it on the matrix.

The temperature for coating is usually about 25 to about 60° C., preferably about 25 to about 40° C.

The time necessary for coating is suitably selected in consideration of the coating method, the properties and amount of the coating agent used, and the properties of the matrix.

The solid preparation may be in any form usable as a nasal agent, and the form of the preparation includes e.g. finely divided particles, powder and granules. In particular, finely divided particles and powder are preferable.

The particle diameters of the finely divided particles are distributed such that for example, 75 to 500 μm particles account for 85 weight % or more, 500 to 850 μm particles for 5 weight % or less, 850 μm or more particles for 0 weight %, and 74 μm or less particles for 10 weight % or less.

The particle diameters of the powder are distributed such that for example, 500 to 850 μm particles account for 5 weight % or less, 500 μm or less particles for 95 weight % or more, and 850 μm or more particles for 0 weight %.

The particle diameters of the granules are distributed such that for example, 500 to 1410 μm particles account for 90 weight % or more, and 177 μm or less particles for 5 weight % or less.

The solid preparation is preferably in a particle form, more preferably in a spherical form. The particle diameter is selected from the range where the solid preparation can be used as a nasal agent. The particle diameter of the solid preparation is preferably about 0.1 to about 1500 μm, more preferably about 0.1 to about 100 μm and most preferably about 5 to about 50 μm.

The most preferable form of using the matrix adhering to the nasal mucosa according to this invention is a preparation for nasal administration (preferably a spray) obtained by encapsulating the solid preparation (preferably finely divided particles or powder) obtained in the manner described above, together with additives such as a stabilizer, a taste corrective, a suspending agent, an emulsifier, a perfume, a dispersant and a lubricant, into a suitable vessel and then sealing the vessel. Preferably, the jetted form of the spray is for example in the form of spray, paste, foam or powder, and the powdery form is particularly preferable.

The matrix adhering to the nasal mucosa according to this invention may be used after it is dissolved, suspended or emulsified in an aqueous solvent (for example, distilled water, physiological saline, Ringer's solution) or an oil solvent (for example, vegetable oils such as olive oil, sesame oil, cottonseed oil and corn oil; propylene glycol etc.).

The matrix adhering to the nasal mucosa according to this invention is low-toxic and safely administered via the nose into mammals (for example, humans, monkeys, dogs, cats, rabbits, cattle, horses, goats, rats, mice etc.).

The dose of the matrix adhering to the nasal mucosa according to this invention may be suitably determined in consideration of the type of the drug, the subject of administration, etc. For example, when the matrix adhering to the nasal mucosa according to this invention is administered as a spray into an adult (weighing about 50 kg) for the purpose of preventing and treating diseases such as encephalomyelitis etc., the daily dose of the matrix adhering to the nasal mucosa is usually about 1 to about 2000 mg and preferably about 20 to about 600 mg, more preferably about 20 to about 200 mg (or about 1 to about 1500 mg, preferably about 20 to about 500 mg and more preferably about 20 to 150 mg in terms of the drug). This dose may be administered in one to three portions.

The diseases to which the matrix adhering to the nasal mucosa according to this invention is applied are selected depending on the type of "the drug exerting its effect in the brain".

BEST MODE FOR CARRYING OUT THE INVENTION

Hereinafter, this invention is described in more detail by reference to the Examples, which however are not intended to limit this invention.

EXAMPLES

Example 1

7.0 g behenic acid hexa(tetra)glyceride (trade name: HB-310, produced by Sakamoto Yakuhin Kogyo Co., Ltd.) and 1.0 g hardened sesame oil [trade name: Lovely Wax 101 (LW-101) produced by Freund Industrial Co., Ltd.] were weighed and melted by heating at 84° C. To the resulting molten mixture were added 1.0 g cephalexin and 1.0 g acrylate type polymer (trade name: HIVISWAKO 104 produced by Wako Pure Chemical Industries, Ltd.) in succession, and the mixture was kept at 84° C. for 15 minutes under stirring. The resulting molten mixture was dropped at a rate of 10 g/min. onto an aluminum disk of 15 cm in diameter rotating at 9000 rpm, to give 6.8 g powder (spherical particles) having a diameter of about 50 μm.

Example 2

8.0 g behenic acid hexa(tetra)glyceride (trade name: HB-310, produced by Sakamoto Yakuhin Co., Ltd.) was weighed and melted by heating at 84° C. 1.0 g (S)-N-[2-(1,6,7,8-tetrahydro-2H-indeno [5,4-b]furan-8-yl)ethyl] propionamide (Compound A) and 1.0 g acrylate type polymer (trade name: HIVISWAKO 104, Wako Pure Chemical Industries, Ltd.) were added thereto in succession, and the mixture was dispersed by keeping it at 84° C. for about 1 hour under stirring. The resulting molten mixture was dropped at a rate of 10 g/min. onto an aluminum disk of 15 cm in diameter rotating at 9000 rpm, to give about 50 μm spherical particles.

Experimental Example 1

10 mg of the particles (cephalexin content: 1 mg) obtained in Example 1 was charged into a polyethylene tube having an inner diameter of 0.58 mm and an outer diameter of 0.965 mm [trade name: PE50; produced by Nippon Becton Dickinson Ltd.], and the total amount of the powder in the tube was administered into the nasal cavity of each SD rat (9- to 10-week-old male) under anesthesia with ether.

Separately, 20 μl aqueous suspension of cephalexin (cephalexin content: 1 mg) was administered into the nasal cavity of each SD rat (9- to 10-week-old male) under anesthesia with ether, and this rat was used as the control.

One hour after administration, the concentrations of cephalexin in plasma and cerebrospinal fluid were measured by HPLC. The results are shown in Table 1.

Each concentration in the table shows an average concentration obtained using 4 rats.

TABLE 1

|  | Concentration in plasma (µg/ml) | Concentration in cerebrospinal fluid (µg/ml) |
|---|---|---|
| Suspension | 0.89 | 0.037 |
| Powder in Example 1 | 0.77 | 0.326 |

As shown in Table 1, when the preparation of this invention was administered via the nose into the rat, the concentration of the drug in the cerebrospinal fluid was significantly higher than by the control suspension. That is, transfer of the drug into the brain was improved by the preparation of this invention.

Experimental Example 2

The particles obtained in Example 2 was charged into a polyethylene tube having an inner diameter of 0.58 mm and an outer diameter of 0.965 mm [trade name: PE50, produced by Nippon Becton Dickinson Ltd.], and then administered in a dose of 3 mg/rat into the nasal cavity of each SD male rat under anesthesia with ether. As the control, 25 µl suspension of Compound A was administered into the nasal cavity of each rat. The concentration of the drug in plasma for 2 hours after administration was measured, and its AUC was calculated. Further, the concentration of the drug in cerebrospinal fluid at 2 hours after administration was measured as an indicator of transfer of the drug into the brain. The results are shown in Table 2.

TABLE 2

|  | $AUC_{0-2h}$ (µg/ml) | Concentration in cerebrospinal fluid (ng/ml) |
|---|---|---|
| Suspension | 1.57 | 9 |
| Particles in Example 2 | 1.78 | 54 |

As shown in Table 2, when the preparation of this invention was administered via the nose into the rat, the concentration of the drug in the cerebrospinal fluid was significantly higher than by the control suspension. That is, transfer of the drug into the brain was improved by the preparation of this invention.

INDUSTRIAL APPLICABILITY

When "the drug exerting its effect in the brain" is orally administered, transfer of said drug into the brain is significantly restricted due to degradation with gastric acid or enzyme, metabolism by the first pass effect, etc. Further, when "the drug exerting its effect in the brain" is subcutaneously or intravenously administered, transfer of said drug into the brain is significantly restricted by the blood-brain barrier.

By using the matrix adhering to the nasal mucosa according to this invention, "the drug exerting its effect in the brain" in said matrix can, without undergoing the above restriction, be transferred directly from the nasal cavity via the cerebrospinal fluid to brain tissues, thus achieving extremely high transfer of said drug into the brain.

Furthermore, the matrix adhering to the nasal mucosa according to this invention is excellent in adhesion to the nasal mucosa and can be retained on the nasal mucosa for a prolonged period of time, thus allowing "the drug exerting its effect in the brain" to be supplied continuously into the brain for a prolonged period of time.

What is claimed is:

1. A matrix adhering to the nasal mucosa which allows improved transfer into the brain of a drug exerting its effect in the brain, which comprises a polyglycerol fatty acid ester, the drug exerting its effect in the brain, and a viscogenic substance, wherein the drug exerting its effect in the brain is (S)-N-[2-(1,6,7,8-tetrahydro-2H-indeno [5,4-b]furan-8-yl) ethyl] propionamide.

2. A matrix adhering to the nasal mucosa which allows improved transfer into the brain of a drug exerting its effect in the brain, which comprises a polyglycerol fatty acid ester, the drug exerting its effect in the brain, and a viscogenic substance, wherein the drug exerting its effect in the brain is (S)-N-[2-(1,6,7,8-tetrahydro-2H-indeno [5,4-b]furan-8-yl) ethyl] acetamide.

* * * * *